United States Patent [19]

Aasen et al.

[11] Patent Number: 4,752,633

[45] Date of Patent: Jun. 21, 1988

[54] ETHOXYLATED SILOXANE SURFACTANTS AND HYDROPHILIC SILICONES PREPARED THEREWITH

[75] Inventors: Steven M. Aasen, Lakeland; Thomas T. Bryan, Mahtomedi, both of Minn.

[73] Assignee: Minnesota Mining and Manufacturing Co., St. Paul, Minn.

[21] Appl. No.: 58,516

[22] Filed: Jun. 5, 1987

Related U.S. Application Data

[62] Division of Ser. No. 798,738, Nov. 15, 1985, Pat. No. 4,691,039.

[51] Int. Cl.$^4$ ............................................. C08K 5/24
[52] U.S. Cl. ..................... 524/266; 264/16; 264/18; 264/19; 433/214; 524/588; 524/730; 524/731; 524/858; 524/859; 524/860; 524/861; 556/446
[58] Field of Search ............... 556/446; 524/266, 588, 524/730, 731, 858, 859, 860, 861; 264/16, 18, 19; 433/214

[56] References Cited

U.S. PATENT DOCUMENTS

| | | |
|---|---|---|
| Re. 25,727 | 2/1965 | Haluska ........................... 260/448.2 |
| 3,057,901 | 10/1962 | Plueddemann ................... 260/448.2 |
| 3,398,104 | 8/1968 | Haluska ............................. 260/2.5 |
| 3,402,192 | 9/1968 | Haluska ........................... 260/448.2 |
| 3,505,377 | 4/1970 | Morehouse ...................... 260/448.2 |
| 3,560,544 | 2/1971 | Haluska ........................... 260/448.2 |
| 3,929,509 | 12/1975 | Taskier ............................... 136/146 |
| 3,980,688 | 9/1976 | Litteral et al. .................... 260/448.2 |
| 4,160,776 | 7/1979 | Scardera et al. ................. 260/448.2 |
| 4,226,794 | 10/1980 | Sacrdera et al. ..................... 556/443 |
| 4,259,467 | 3/1981 | Keogh et al. ......................... 526/279 |
| 4,332,922 | 6/1982 | Kossmehl et al. .................. 525/478 |
| 4,337,168 | 6/1982 | Scardera et al. .................... 252/312 |
| 4,354,873 | 10/1982 | Supcoe et al. .................... 106/18.32 |
| 4,395,454 | 7/1983 | Baldwin ............................... 428/290 |
| 4,414,660 | 11/1983 | Wang et al. .......................... 369/286 |
| 4,431,789 | 2/1984 | Okazaki et al. ....................... 528/15 |
| 4,468,491 | 8/1984 | Steinberger et al. ................ 524/493 |
| 4,510,227 | 4/1985 | Mohr et al. ........................... 430/175 |
| 4,517,240 | 5/1985 | Tracton et al. ....................... 428/326 |
| 4,657,959 | 4/1987 | Bryan et al. ........................... 524/266 |
| 4,691,039 | 9/1987 | Aasen et al. .......................... 556/446 |

OTHER PUBLICATIONS

Noll, W., "Chemistry and Technology of Silicones", 447–452 at 448 (1982).
Scott, G., Englebrecht, L., and Holdt, H. J., *Z. anorg. allg. Chem.*, 459, 177–186 (1979).
Vick, S. C., "Structure/Property Relationships for Silicone Polyalkyleneoxide Copolymers and Their Effect on Performance in Cosmetics", *Soap/Cosmetics/Chemical Specialties*, 60, (5), 36 (May 1984).
"Organomodified Oils [OMO]" (Product Literature from Union Carbide Corp., dated Apr. 1982).
"Silicate Cluster Fluids" (Product Literature from Olin Corp.).
"Silicones", *Kirk Othmer Encyclopedia of Chemical Technology*, 3rd Ed., 20, 922–962.
"Silwet ® Surface Active Copolymers" (Product Literature from Union Carbide Corp., dated Oct. 1983).
"UCARSIL ® EPS Silicone Hydrophilic Finish" (Product Literature from Union Carbide Corp., dated Mar., 1984).
Lacy, A., Treleaven, S. and Jendresen, M. "The Effect of Selected Surfactants on the Wetting Behavior of Gypsum Die Stone on Impression Materials", *Cal. Dent. Assn. J.*, 5:36–40 (1977).
Norling, D. K. and Reisbick, M. H., "The Effect of Nonionic Surfactants on Bubble Entrapment in Elastomeric Impression Materials", J. Pros. Dent., 42:342–347 (Sep., 1979).

Primary Examiner—Melvyn I. Marquis
Attorney, Agent, or Firm—Donald M. Sell; James A. Smith; David R. Cleveland

[57] ABSTRACT

Ethoxylated siloxane surfactants, and mixtures of such surfactants with curable silicone prepolymers. The mixtures are hydrophilic after cure, have semipermanent hydrophilicity, and are especially useful as dental impressions.

7 Claims, No Drawings

ETHOXYLATED SILOXANE SURFACTANTS AND HYDROPHILIC SILICONES PREPARED THEREWITH

This is a division of application Ser. No. 798,738, filed Nov. 15, 1985, now U.S. Pat. No. 4,691,039.

TECHNICAL FIELD

This invention relates to novel siloxane surfactants. This invention also relates to curable silicone prepolymer compositions and cured silicone polymers. In another aspect, this invention relates to molded silicone articles. In a further aspect, this invention relates to dental impression materials.

BACKGROUND ART

Many different substances have been used as dental impression materials, each having its own advantages and disadvantages. An impression material must undergo a transformation, while in the mouth, from a viscous liquid to a rubbery solid. While factors such as taste, odor, toxicity, viscosity, cure speed, ease of demolding and strength after cure are all important, accuracy is of paramount concern. An impression material must accurately replicate the shape, size, and relative locations of both hard and soft tissues within the mouth. After cure, the impression must enable casting ("pouring") of an accurate model. The model usually is a plaster of Paris "stone" prepared from an aqueous gypsum slurry, which after setting represents a positive mold of the mouth. In recent years, silicones of both the condensation cure and addition cure varieties have become widely used as impression materials. They exhibit very good accuracy, together with an absence of taste and odor, easy demolding and other properties generally equivalent to or better than other commonly-used impression materials. However, silicone impression materials suffer from the disadvantage of hydrophobicity. This causes inaccurate impressions in moist fields, and discourages thorough wetting and accurate replication when the model is poured. In an attempt to provide better wetting of the impression by the gypsum slurry, some dental laboratories spray the cured impression with a detergent solution just prior to pouring the model.

Repeated attempts have been made to render silicones more hydrophilic by chemically modifying the siloxane backbone or by appending to the backbone various functional groups. Typical approaches are described in U.S. Pat. Nos. 4,259,467 (and in many of the references cited therein) and 4,332,922.

Siloxanes have been used as surface active agents, emulsifiers, defoamers or coatings, see, e.g. U.S. Pat. Nos. 3,057,901, 3,398,104, 3,402,192, 3,505,377, 3,560,544, 3,929,509, 3,980,688, 4,160,776, 4,226,794, 4,337,168, 4,395,454, 4,414,660, 4,431,789, 4,468,491, 4,510,227, 4,517,240 and Re 25,727. Other publications describing the properties of siloxanes include "Silwet ® Surface Active Copolymers" (product literature from Union Carbide Corp., dated October, 1983), "Organomodified Oils [OMO]" (product literature from Union Carbide Corp., dated April, 1982), "UCAR-SIL ® EPS Silicone Hydrophilic Finish" (product literature from Union Carbide Corp., dated March, 1984), "Silicate Cluster TM Fluids" (product literature from Olin Corp.), and Vick, S. C., "Structure/Property Relationships for Silicone Polyalkyleneoxide Copolymers and Their Effects on Performance in Cosmetics", *Soap/Cosmetics/Chemical Specialties*, 60 (5), 36 (May, 1984).

U.S. Pat. No. 4,354,873 describes an antifouling coating for application to submerged boat hulls. The coating contains fumed silica, silicone oil, antifoulant, and an anionic, nonionic or amphoteric surfactant.

DISCLOSURE OF INVENTION

None of the above patents or publications disclose or suggest combination of a curable silicone prepolymer and a surfactant. The present invention provides, in one aspect, certain novel ethoxylated siloxane surfactants which impart hydrophilicity to cured silicone polymers. The novel surfactants have the average formula:

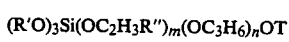

$$(R'O)_3Si(OC_2H_3R'')_m(OC_3H_6)_nOT$$

where each R' group is independently a monovalent hydrocarbyl radical with the proviso that at least a majority of said R' groups are sterically hindered alkyl radicals having at least three carbon atoms, each R" group is independently hydrogen or a lower hydroxyalkyl radical, m is at least one, n is greater than or equal to zero, and T is hydrogen, a monovalent alkyl or alkenyl radical, or a group of the formula $-Si(OR')_3$.

In another aspect, the present invention provides a curable silicone composition comprising a mixture of (a) curable silicone prepolymer and (b) the above-described surfactant, wherein said surfactant is present in sufficient amount, m has a sufficient value, and n is small enough so that said composition, when cured, has a three minute water contact angle below about 65°. The cured composition is readily wet by water, yet retains the other desirable properties characteristic of silicones. The composition facilitates the making of more accurate dental impressions and the pouring of more accurate models.

The present invention also provides molded hydrophilic silicone articles prepared by shaping and curing such a composition. Such articles include dental impressions, lithographic plates, release liners, reflective sheeting, adhesives, coatings and sealants.

In addition, the present invention provides a method for making a dental impression, comprising the step of making a negative model of oral tissue using such a composition.

DETAILED DESCRIPTION

In the practice of the present invention, the curable silicone composition can be a one-part or multiple-part composition cured by the presence of adventitious moisture, crosslinking agents, catalysts, and/or heat. Most preferred are two-part addition cure or condensation cure compositions of the room temperature vulcanizing ("RTV") variety. The composition contains a "curable silicone prepolymer", that is, a polysiloxane having one or more functional groups which enable the prepolymer to be polymerized or cured to a state of higher molecular weight. Suitable silicone prepolymers are well-known in the art and are described, for example, in "Silicones", *Kirk-Othmer Encyclopedia of Chemical Technology*, 3rd Ed., 20, 922–962 (1982), the disclosure of which is incorporated herein by reference.

The surfactant contains one or more siloxane solubilizing groups which render the surfactant soluble or dispersible in the silicone prepolymer. The surfactant also contains one or more water-loving groups which render a cured composition of the invention hydrophilic. The water-loving groups are ethyleneoxy (—$C_2H_4O$—) groups or hydroxyalkyl-substituted ethyleneoxy (e.g., —$CH_2CH(CH_2OH)O$—) groups. For brevity, these water-loving groups will sometimes be collectively referred to hereafter as "ethyleneoxy" groups.

The ethyleneoxy group(s) can be attached to the siloxane solubilizing group through either end of an ethyleneoxy group, that is, through a carbon atom or an oxygen atom of the ethyleneoxy group. The surfactant preferably contains at least four ethyleneoxy groups (that is, the subscript m in the formula shown above preferably is at least four), and more preferably it contains at least ten to twenty such groups. The number of ethylenoxy groups should not be so large that the surfactant becomes waxy, as that may reduce its effectiveness. The surfactant also can contain other groups or substituents, if present in types and amounts which do not interfere with the functioning of such surfactant in the present invention or with the curing of the silicone prepolymer. Examples of such groups include propyleneoxy (—$C_3H_6O$—), vinyl, —$NH_2$, —SH and oxirane groups. In the formula shown above, it is also preferred that R' is sec-butyl, R" is hydrogen, n is zero and T is —Si(sec-butoxy)$_3$.

The compounds of the invention are conveniently prepared by reacting a trialkoxyhalosilane with an alkoxylated linear alcohol or diol. This preparation can be carried out by modifying the procedures shown in U.S. Pat. Nos. 4,160,776 and 4,226,794 (the disclosures of which are incorporated herein by reference), substituting the trialkoxyhalosilane for the bis(trialkoxysiloxy)alkylhalosilane used in these patents. The resulting compound is a surfactant which can be used for the same purposes as the surfactant compounds described in these patents. An additional (and preferred) use for the surfactants of the present invention is in compositions containing such surfactants together with a curable silicone prepolymer. The resulting compositions exhibit hydrophilicity when cured. Such hydrophilicity is manifested by a reduction in the contact angle formed by a drop of water when it is placed on a cured sample of a composition of the invention.

The surfactant is present in a sufficient amount and contains a sufficient number of ethyleneoxy groups so that the silicone composition, when cured, has a three minute water contact angle below about 65°. The term "three minute water contact angle" refers to the contact angle formed by a drop of distilled water three minutes after it is applied to a cured composition of the invention, as measured at room temperature using a goniometer. Such contact angle measurements can be made as described in Noll. W., "Chemistry and Technology of Silicones", 447–452 at 448 (1982). Preferably, such measurements are conducted by curing a composition of the invention against a smooth substrate (e.g., a glass sheet), separating the substrate and silicone after cure, and placing the water drop on the smooth cured surface of the silicone. Preferably, the compositions of the invention have a three minute water contact angle below about 45°.

The measured contact angle appears to be strongly dependent upon the amount of surfactant and the number of ethylenoxy groups present within the surfactant. In general, as the amount of surfactant increases, the water contact angle decreases. In general, as the number of ethyleneoxy groups increases beyond one, the water contact angle decreases to a minimum and then increases. The number of ethyleneoxy groups which provides the desired three minute water contact angle will vary depending upon several other factors, including the remaining substituent groups present in the surfactant. The effect of such other factors is illustrated in the examples set forth below. For example, the water contact angle tends to increase if propyleneoxy groups are present in the surfactant. Preferably no propyleneoxy groups are present in such surfactant.

It has also been found that the measured water contact angle increases if a cured composition is immersed in running water for a prolonged period of time. Without intending to be bound by theory, it is believed that the surfactant is dissolved or dispersed throughout the cured compositions of the invention and can migrate therein and into adjacent fluids. When a drop of water is placed on a cured composition of the invention, it is believed that the surfactant migrates into the drop and reduces the interfacial surface tension between the water and the silicone. This hypothesis is supported by the above-noted increase in water contact angle after prolonged water exposure, and by two additional observations. First, the measured water contact angle slowly changes after the drop is placed on the surface of the cured silicone, generally reaching an equilibrium after about five minutes. Second, if the drop is observed using an optical comparator (which provides a highly magnified view of the drop), schlieren patterns become visible at the interface between the drop and the silicone within a few seconds after the drop is applied. As this takes place, the schlieren patterns diffuse throughout the drop and the drop slowly collapses and spreads out on the surface of the silicone.

In view of the above, the cured compositions of the invention perhaps are best regarded as having semipermanent hydrophilicity, that is, their hydrophilicity is subject to diminution upon prolonged contact with water. This dimunition is not a material drawback when making dental impressions, since the amount of water or other fluids which will come into contact with the impression is not excessive and in any event somewhat predictable in advance. A similar observation can be made in regard to other applications for the cured compositions of the invention (e.g., lithographic plates, release liners, reflective sheeting, adhesives, coatings and sealants). Additional applications for the compositions of the invention such as contact and intraocular lenses, silicone implants (e.g. artificial veins or mammary implants), and wound dressings may be possible, but would be contraindicated somewhat due to the longerterm fluid exposure involved and the possible adverse effects of surfactant migration.

As pointed out above, when the amount of surfactant is increased, the three minute water contact angle generally decreases. As the amount of surfactant is increased further, the three minute contact angle reaches a minimum threshold value which does not decrease significantly with the use of additional surfactant. In general, a preferred amount of surfactant is an amount sufficient to provide a three minute water contact angle having such minimum threshold value. This preferred amount of surfactant also depends upon the particular curable silicone prepolymer chosen, the particular surfactant chosen, and the amounts and types of other adjuvants present in the compositions of the invention. Expressed on a weight basis, an effective amount of surfactant preferably is below about 30 weight percent, based on the total weight of the composition. More preferably, the amount of surfactant is about 0.25 to five weight percent, and most preferably about 0.5 to two weight percent.

The compositions of the invention are mixed, packaged and stored like conventional curable silicone compositions. In two-part compositions, the surfactant usually can be present in either part of the composition, or in both parts of the composition. However, where the surfactant may tend to react with either part of the composition (e.g., if the surfactant contains one or more Si-H groups, and will be used in an addition cure polysiloxane), then the surfactant should be added only to a part of the composition with which it will not itself react. Mixtures of more than one surfactant can be used if desired.

The compositions of the invention can also contain adjuvants of the type customarily employed in curable silicone compositions. Such adjuvants include crosslinking agents, catalysts, fillers, pigments, reinforcing agents, plasticizers and the like.

The invention is illustrated in the following examples, in which all parts and percentages are by weight unless otherwise indicated. Because the examples are merely illustrative, they are not to be construed as limiting the scope of the invention.

PREPARATORY EXAMPLE 1

A two-part vinylpolysiloxane impression material of the following formulation was prepared:

| Catalyst part: | |
|---|---|
| Vinyl-terminated polydimethylsiloxane, $M_n = 24,000$ | 46.3% |
| Silicone-treated silica[1] | 6.1 |
| Ground silica[2] | 46.9 |
| Catalyst made from a 2:1 mixture of 1,3-divinyl tetramethyl disiloxane and chloroplatinic acid | 0.7 |
| Base part: | |
| Vinyl-terminated polydimethylsiloxane, $M_n = 24,000$ | 42.4% |
| Silicone-treated silica[1] | 7.3 |
| Ground silica[2] | 46.6 |
| Silicone crosslinking agent[3] | 3.7 |
| Tetravinyltetramethylcyclotetrasiloxane | 0.06 |

[1]"QUSO 545", Philadelphia Quartz.
[2]"IMSIL A-25", Illinois Minerals.
[3]A copolymer which on the basis of monomers charged would have an average composition $MD'_{10}D_{21}M$ where
$M = Si(CH_3)_3O_{0.5}$
$D = Si(CH_3)_2O$
$D' = Si(CH_3)HO$.

In the examples which follow, various surfactants were added to both parts of the above formulation. The two parts were then combined in equal proportions, mixed rapidly, poured into a cylindrical metal mold 19 mm in diameter × 1 mm in thickness sandwiched between two glass microscope slides, and allowed to cure for ten minutes at room temperature. A drop of distilled water was carefully placed on the cured surface and the contact angle formed by the drop was measured using a goniometer 30 seconds and three minutes after placement of the water drop.

EXAMPLE 1

Tri(sec-butoxy)chlorosilane was prepared according to the procedure described in Schott, G., Englebrecht, L., and Holdt, H. J., *Z. anorg. allg. Chem.*, 459, 177–186 (1979). A 56.5 g portion of the resulting product was added dropwise to a stirred solution of 60 g of a polyethyleneglycol having the average formula $HO(C_2H_4O)_{13.2}H$ ("Carbowax 600", Union Carbide Corp.) and 16 g pyridine in 300 ml toluene. The resulting mixture was heated to 70° C. for two hours, then allowed to cool to room temperature and filtered to remove pyridine hydrochloride. Toluene was removed from the mixture using a rotary evaporator. Final traces of toluene and unreacted pyridine were removed under high vacuum ($10^{-2}$ Torr). The product was a clear, colorless to faint yellow fluid. NMR and IR analyses were consistent with the average structure (sec-butoxy)$_3$SiO(C$_2$H$_4$O)$_{13.2}$Si(sec-butoxy)$_3$. Using $^1$H NMR analysis with CDCl$_3$ as solvent, delta values were 0.90(18H,d,—CHC$\underline{H}_3$), 1.17 (18H,t,—CH$_2$C$\underline{H}_3$), 1.45 (12H,q,—C$\underline{H}_2$CH$_3$), 3.61 (53H,s,OC$\underline{H}_2$CH$_2$), and 3.87 (6H,—C$\underline{H}$). Using IR analysis, absorption peaks occurred at 2898, 1485, 1379, 1351, 1330, 1299, 1258, 1117, 1058, 1018, 960, 862, 816 and 735 cm$^{-1}$.

When one percent of this novel ethoxylated surfactant was added to both parts of the impression material formulation of PREPARATORY EXAMPLE 1, the cured composition had 30 second and three minute water contact angles of 44° and 32°, respectively. If the surfactant was excluded, the cured composition had 30 second and three minute water contact angles of 100° and 99°, respectively.

This example illustrates the reduction in water contact angle (and the increase in hydrophilicity) that is obtained when a small amount of a surfactant of the invention is used in a composition of the invention.

EXAMPLE 2

Using the method of EXAMPLE 1, and substituting a variety of alkoxylated linear alcohols or diols for the polyethyleneglycol used in EXAMPLE 1, a series of novel alkoxylated surfactants having the average formula (R'O)$_3$Si(OC$_2$H$_4$)$_m$(OC$_3$H$_6$)$_n$OT were synthesized. Using the method of EXAMPLE 1, one percent of each of these surfactants was added to both parts of the impression material formulation of PREPARATORY EXAMPLE 1. Set out below in TABLE I are the run number, identity of R', m, n and T, and the equilibrium water contact angle for each composition. Water contact angles measured at three minutes would be the same or only slightly different from the equilibrium water contact angles.

TABLE I

| Run no. | R' | m | n | T | Equilibrium water contact angle |
|---|---|---|---|---|---|
| 1 | sec-butyl | 2 | 0 | —CH$_3$ | 90° |
| 2 | sec-butyl | 7.2 | 0 | —CH$_3$ | 56° |
| 3 | sec-butyl | 11.8 | 0 | —CH$_3$ | 72° |
| 4 | sec-butyl | 16.3 | 0 | —CH$_3$ | 84° |
| 5 | sec-butyl | 42.5 | 0 | —CH$_3$ | 98° |
| 6 | sec-butyl | 3 | 0 | T'[1] | 76° |
| 7 | sec-butyl | 6.4 | 0 | T' | 63° |
| 8 | sec-butyl | 8.7 | 0 | T' | 57° |
| 9 | sec-butyl | 13.2 | 0 | T' | 36° |
| 10 | sec-butyl | 22.3 | 0 | T' | 59° |
| 11 | sec-butyl | 0 | 16.9 | T' | 71° |
| 12 | sec-butyl | 0 | 18.8 | T' | 66° |
| 13 | sec-butyl | 0 | 34.2 | T' | 73° |
| 14 | sec-butyl | 0 | 51.4 | T' | 76° |
| 15 | (2) | 7.2 | 0 | —CH$_3$ | 44° |
| 16 | (2) | 16.3 | 0 | —CH$_3$ | 59° |
| 17 | (2) | 13.2 | 0 | T"[3] | 85° |
| 18 | (2) | 22.3 | 0 | T" | 76° |

[1]T' = —Si(sec-butoxy)$_3$.
[2]Two sec-butoxy groups and one allyloxy group were attached to the Si atom shown in the formula.
[3]T" = —Si(sec-butoxy)$_2$(allyloxy).

This example shows several novel surfactants, and the effect variation in their structure has upon the hydrophilicity of a cured composition of the invention.

COMPARATIVE EXAMPLE 1

A series of silicate "cluster" surfactants having the following average formula were synthesized using the method shown in Example 1 of U.S. Pat. No. 4,226,794:

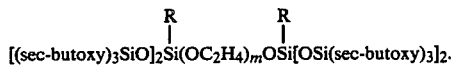

[(sec-butoxy)$_3$SiO]$_2$Si(OC$_2$H$_4$)$_m$OSi[OSi(sec-butoxy)$_3$]$_2$.

One percent of each of these surfactants added to both parts of the impression material formulation of PREPARATORY EXAMPLE 1. Set out below in TABLE II are the run number, identity of R and m, and the equilibrium water contact angle for each composition.

TABLE II

| Run no. | R | m | Equilibrium water contact angle |
|---|---|---|---|
| 1 | H— | 13.2 | 52° |
| 2 | CH$_3$— | 3.0 | 92° |
| 3 | CH$_3$— | 8.7 | 65° |
| 4 | CH$_3$— | 13.2 | 56° |
| 5 | CH$_2$=CH— | 13.2 | 66° |
| 6 | CH$_2$=CH— | 34.6 | 59° |

An additional series of silicate "cluster" surfactants of the following average formula was synthesized using the method shown in Example 2 of U.S. Pat. No. 4,160,776:

[(sec-butoxy)$_3$SiO]$_2$Si(OC$_2$H$_4$)$_m$OCH$_3$.

One percent of each of these surfactants was added to both parts of the impression material formulation of PREPARATORY EXAMPLE 1. Set out below in TABLE III are the run number, identity of R and m, and the equilibrium water contact angle for each composition.

TABLE III

| Run no. | R | m | Equilibrium water contact angle |
|---|---|---|---|
| 1 | H— | 7.2 | 39° |
| 2 | CH$_3$— | 7.2 | 31° |
| 3 | CH$_3$— | 11.8 | 32° |
| 4 | CH$_3$— | 16.3 | 37° |
| 5 | CH$_2$=CH— | 2.0 | 88° |
| 6 | CH$_2$=CH— | 7.2 | 49° |
| 7 | CH$_2$=CH— | 11.8 | 28° |
| 8 | CH$_2$=CH— | 42.5 | 100° |

This comparative example shows the water angle values obtained when several surfactants of U.S. Pat. Nos. 4,160,776 and 4,226,794 are used in a curable silicone composition. Comparison of these values to those shown above demonstrates that the compounds of the invention provide a comparable degree of hydrophilicity in a cured silicone composition.

Various modifications and alterations of this invention will be apparent to those skilled in the art without departing from the scope and spirit of this invention and the latter should not be restricted to that set forth herein for illustrative purposes.

We claim:

1. A curable silicone composition, comprising a mixture of (a) curable silicone prepolymer and (b) ethoxylated surfactant having the average formula:

(R'O)$_3$Si(OC$_2$H$_3$R")$_m$(OC$_3$H$_6$)$_n$OT wherein each R' group is independently a monovalent hydrocarbyl radical with the proviso that at least a majority of said R' groups are sterically hindered alkyl radicals having at least three carbon atoms, each R" group is independently hydrogen or a lower hydroxyalkyl radical, m is at least one, n is greater than or equal to zero, and T is hydrogen, a monovalent alkyl or alkenyl radical, or a group of the formula —Si(OR')$_3$, and wherein said surfactant is present in sufficient amount, m has a sufficient value, and n is small enough so that said composition, when cured, has a three minute water contact angle below about 65°.

2. A composition according to claim 1, wherein said curable silicone prepolymer comprises a two-part RTV addition cure or condensation cure polysiloxane.

3. A composition according to claim 1, wherein said contact angle is below about 45°.

4. A composition according to claim 1, wherein said curable silicone prepolymer comprises a two part RTV addition cure polysiloxane, R' is sec-butyl, R" is hydrogen, m is ten to 20, n is zero, and T is —Si(sec-butoxy)$_3$.

5. A composition according to claim 1, in the form of a cured composition having said surfactant dissolved or dispersed therein, said cured composition comprising a dental impression, said impression comprising a negative mold of oral tissue.

6. A composition according to claim 1, in the form of a cured composition having said surfactant dissolved or dispersed therein, said cured composition comprising a lithographic plate, release liner, reflective sheet, adhesive, coating or sealant.

7. A method for making a dental impression, comprising the step of making a negative mold of oral tissue using as said mold a curable silicone composition comprising a mixture of (a) RTV addition cure or condensation cure polysiloxane prepolymer and (b) ethoxylated surfactant having the average formula:

(R'O)$_3$Si(OC$_2$H$_3$R")$_m$(OC$_3$H$_6$)$_n$OT wherein each R' group is independently a monovalent hydrocarbyl radical with the proviso that at least a majority of said R, groups are sterically hindered alkyl radicals having at least three carbon atoms, each R" group is independently hydrogen or a lower hydroxyalkyl radical, m is at least one, n is greater than or equal to zero, and T is hydrogen, a monovalent alkyl or alkenyl radical, or a group of the formula —Si(OR')$_3$, and wherein said surfactant is present in sufficient amount, m has a sufficient value, and n is small enough so that said composition, when cured, has a three minute water contact angle below about 65°.

* * * * *

UNITED STATES PATENT AND TRADEMARK OFFICE
CERTIFICATE OF CORRECTION

PATENT NO. : 4,752,633
DATED : June 21, 1988
INVENTOR(S) : STEVEN M. AASEN and THOMAS T. BRYAN It is certified that error appears in the above-identified patent and that said Letters Patent is hereby corrected as shown below:

Col. 7, line 58, "water angle" should read --water contact angle--.

Col. 8, line 54, "R," should read --R'--.

Signed and Sealed this

Twenty-fifth Day of April, 1989

*Attest:*

DONALD J. QUIGG

*Attesting Officer*  *Commissioner of Patents and Trademarks*